United States Patent [19]

Peillex

[11] 4,021,878

[45] May 10, 1977

[54] PROTECTING GLASSES

[75] Inventor: Paul Peillex, Thonon les Bains, France

[73] Assignee: Arisara Investment Corporation, Curacao, Netherlands Antilles

[22] Filed: Feb. 4, 1975

[21] Appl. No.: 546,886

[30] Foreign Application Priority Data

| | | |
|---|---|---|
| Mar. 15, 1974 | Switzerland | 3605/74 |
| Feb. 19, 1974 | Switzerland | 2265/74 |

[52] U.S. Cl. .................. 15/250.28; 15/250.29; 15/250.3; 15/250.36; 2/438; 351/158
[51] Int. Cl.² ................. B60S 1/06; B60S 1/44
[58] Field of Search ..... 15/250.28, 250.10, 250.36, 15/250.29; 351/41, 47, 158; 2/438, 435, 427, 428

[56] References Cited

UNITED STATES PATENTS

| | | | |
|---|---|---|---|
| 683,881 | 10/1901 | Kochenderfer | 15/250.28 X |
| 1,189,978 | 7/1916 | Lyon | 15/250.24 X |
| 1,251,036 | 12/1917 | Ilse | 15/250.28 |
| 1,379,232 | 5/1921 | Webb | 15/250.28 |
| 2,329,757 | 9/1943 | Greenfield | 15/250.28 |
| 3,526,920 | 9/1970 | Boyanich, Sr. | 15/250.29 |
| 3,689,136 | 9/1972 | Atamian | 351/47 X |
| 3,789,428 | 2/1974 | Martin | 2/428 |
| 3,890,647 | 6/1975 | Warncke | 15/250.3 |

FOREIGN PATENTS OR APPLICATIONS

| | | | |
|---|---|---|---|
| 795,771 | 1/1936 | France | 351/158 |
| 1,108,504 | 8/1955 | France | 15/250.30 |
| 1,303,305 | 7/1962 | France | 15/250.29 |
| 226,347 | 3/1943 | Switzerland | 2/427 |

*Primary Examiner*—Peter Feldman
*Attorney, Agent, or Firm*—Young & Thompson

[57] ABSTRACT

Protection glasses comprise a screen which is at least partially transparent and that has upper and lower substantially horiziontal edges. At least one movable wiping member wipingly engages at least one face of the screen and slidably engages the upper and lower edges of the screen thereby releasably to retain the wiping member in horizontal sliding engagement with the screen. The screen preferably has at least one flange along at least one of its edges to mount the wiping member. The wiping member can be in the form of a single member that embraces the screen to wipe both sides of the screen, or two members slidable on flanges along both edges of the screen. The screen can be integral with the frame of the glasses.

5 Claims, 13 Drawing Figures

FIG.2
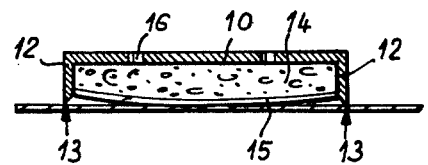
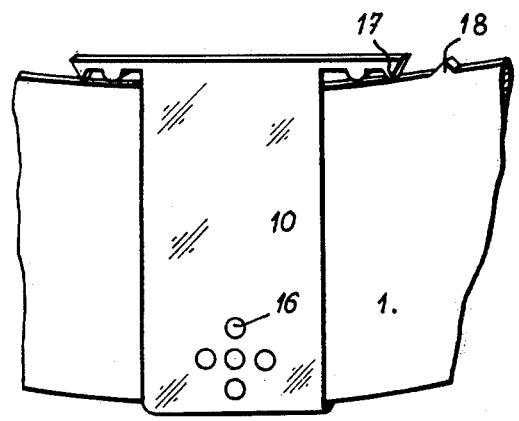
FIG.3

PROTECTING GLASSES

There are numerous protection glasses for sportsmen, particularly for car or motorcycle drivers, skiers and so on, as well as for persons engaging in occupations dangerous to the eyes.

The main drawbacks of these glasses reside in the fact that after a relatively short use they are wetted by the rain or the snow or other projections which reduces the transparency and causes thus an important reduction of the visibility for the persons who wear them.

The present invention has for its object to realize protection glasses which the user may easely clean without having to take them off.

The protection glasses according to the invention comprises a screen at least partially transparent as well as a movable member, displacable with respect to this screen, this member comprising a cleaning device of at least one area of one of the faces of the transparent screen.

The attached drawings show schematically and by way of example embodiments of the portection glasses according to the invention.

FIG. 2 is a transverse cross section of the movable member.

FIG. 3 is a view of a variant of the movable member.

Figure 1:
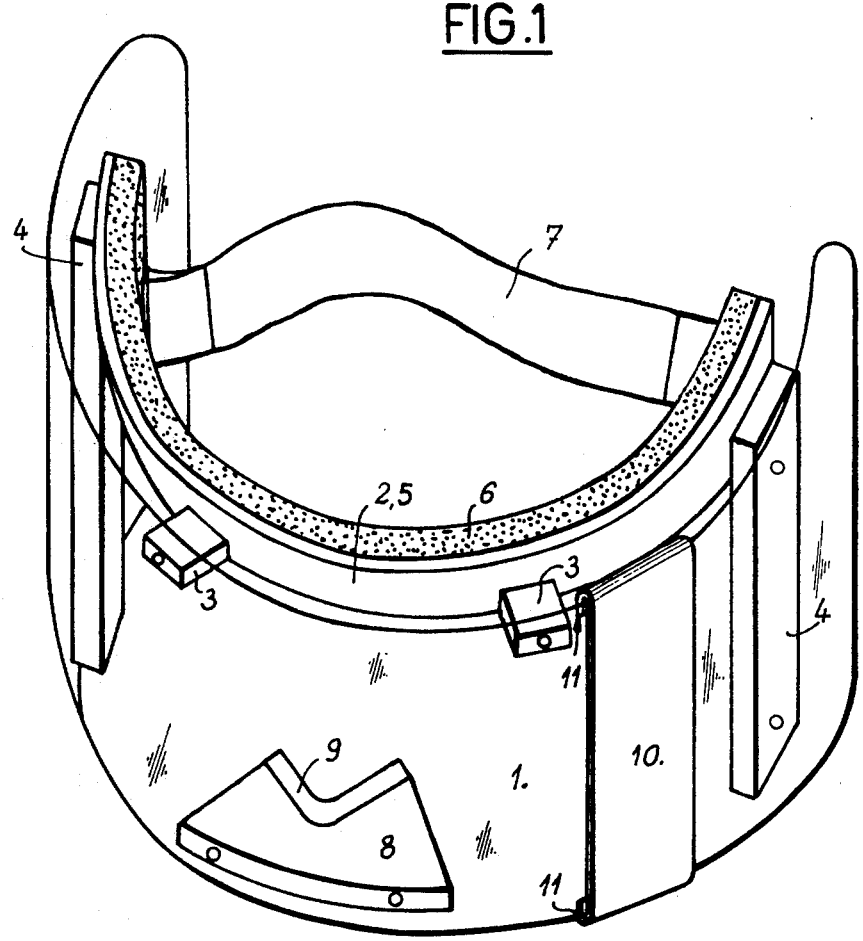
FIG. 1 is a perspective view of the glasses.

In the embodiments shown in FIGS. 1–3, the protection glasses comprises a transparent screen 1, white or coloured, fastened in a fixed or removable way on a support 2 by means of parts 3, 4 located, when the glasses are worn, outside of the vision field of the user.

The support is in the form of an arc 5 provided with a padding 6 in plastic foam for example on its face intended to enter in contact with the head of the user.

A strap or a resilent member 7 fastened at the rear end of the support maintains the glasses in service position.

The screen comprises in its lower portion an abutment 8 intended to enter in contact with the nose of the user to ensure the positioning and the stability of the glasses. This abutment 8 comprises also a padding 9.

For the embodiment shown the screen 1 is constituted by a rectangular strap of transparent plastic material, curved in such a manner as to form a portion of a cylindrical wall.

The upper and lower edges of this screen are parallel to each other.

This protection glasses comprise a movable member constituted by a rider 10 slidably mounted on the screen 1 in a manner to be able to be displaced manually along this screen by the user during the wearing of the glasses. In the embodiment shown the rider 10 presents upper and lower grooves 11 receiving the corresponding edges of the screen.

The rider comprises a cleaning device of at least one zone or area of the screen. This cleaning device may be constituted by a sponge or a padding in supple material such as buckskin, expanded plastic material and so on, located between the rider 10 and the screen 1 and fixed either rigidly or in a removable way into the rider, in such a way that it slides with the rider.

During the relative displacements between the rider and the screen, the sponge or the padding which has been dampened before or impregnated with a cleaning product, cleans the zone of the screen, with which it comes in contact.

The cleaning device may extend full height of the rider 10 and clean nearly the whole surface of the screen or on the contrary it may extend only a part of the height of the rider and thus clean only a portion of the height of the screen.

It is possible to provide abutments limiting the stroke of the rider in order to avoid its being inadvertently separated from the screen during the use of the glasses. These abutments can be removable to enable the deliberate separation of the rider and of the screen in order to clean it or to rinse the cleaning device which is carried by the rider.

In a variant a spring may be placed in one of the grooves of the rider to bear against the corresponding edge of the screen. In this way the rider slides along the screen with little friction and cannot displace itself, but has to be actuated deliberately by the user.

In another variant the rider 10 could completely surround the screen and constitute a ring displacable along said screen. In this case, the rider may present a second cleaning device, similar to the first one but cooperating with the internal face of the screen in order to remove the moisture which can form on this face.

In other variants the upper and lower edges of the screen need not be parallel, for example in the case when the screen would have a shape approximating that of conventional ski glasses. In such embodiments guides could be provided for the sliding of the rider 10. This rider could also comprise within at least one of its grooves 11 a slide coming into contact with the corresponding edge of the screen, subjected to the action of a return spring which compensates for the differences of width of the screen when the rider is displaced along it.

It is evident that in other variants the screen could be fitted in a frame, replacing the shown support, of conventional type, in that case the rider is mounted slidingly on said frame in order to be able to wipe the surface of the screen.

The screen may be of one colour or of several coulours.

The operation of these glasses is very simple. It suffices in fact when the screen is dirty to displace the rider along this screen to clean it. The rider may be removable so that the cleaning device is able to be washed after having been used a certain number of times.

FIG. 2 shows an embodiment of the rider 10 in cross section. The rider or movable member has a profile having the general shape of a U the edges 12 of which have a scraping edge 13 at their end coming in contact with the screen 1. This profile defines a space which is filled with a sponge material 14 such as a sponge or a mass of plastic material, the free surface of which is covered by a buckskin 15 entering into contact with the screen.

The sponge 14 may be wetted with water or with a cleaning product. This cleaning device is particularly efficient due to the combined action of the scraping and the cleaning.

The central portion of the profile 10 comprises holes 16 permitting the flowing out of the water contained in the sponge 14, this evacuation may be facilitated by pressing on the sponge.

In the variant shown in FIG. 3, the rider 10 comprises gripping members 17 intended to cooperate with stops 18 carried by the upper edge of the screen. In this manner it is possible to lock the rider 10 in a rest position to avoid its displacing itself in an unwanted manner. The resiliency of the gripping members 17 permits when an effort is applied to the rider, in the direction of its displacement, the locking and the unlocking of the movable member by passage of these gripping members over the stop 18.

In a variant which has not been shown, the glasses my comprise several riders, particularly two. One of these riders may clean the inside face of the screen while the other one may clean the outside face of said screen. Each rider may also comprise two cleaning devices, one for each face of the screen.

It is evident that the rider may be slidingly guided on the support and not on the screen itself. In such an embodiment, the screen may be mounted in a removable way on the support. One may thus provide for a set of screens of different colours intended to be mounted on a same support.

In a variant, the whole glasses, with the exception of the rider and of the resilent fixing member, may be made out of only one moulding part in plastic material.

The screen may present the shape of a cylindrical portion or of a conical portion, if the radii of its upper and lower edges are identical or not. The plastic material of the screen may be subjected to a treatment in order to increase its hardness in order to avoid scratches. The resilent band or strap 7 may be fixed either on the screen or on the support.

Figure 4:
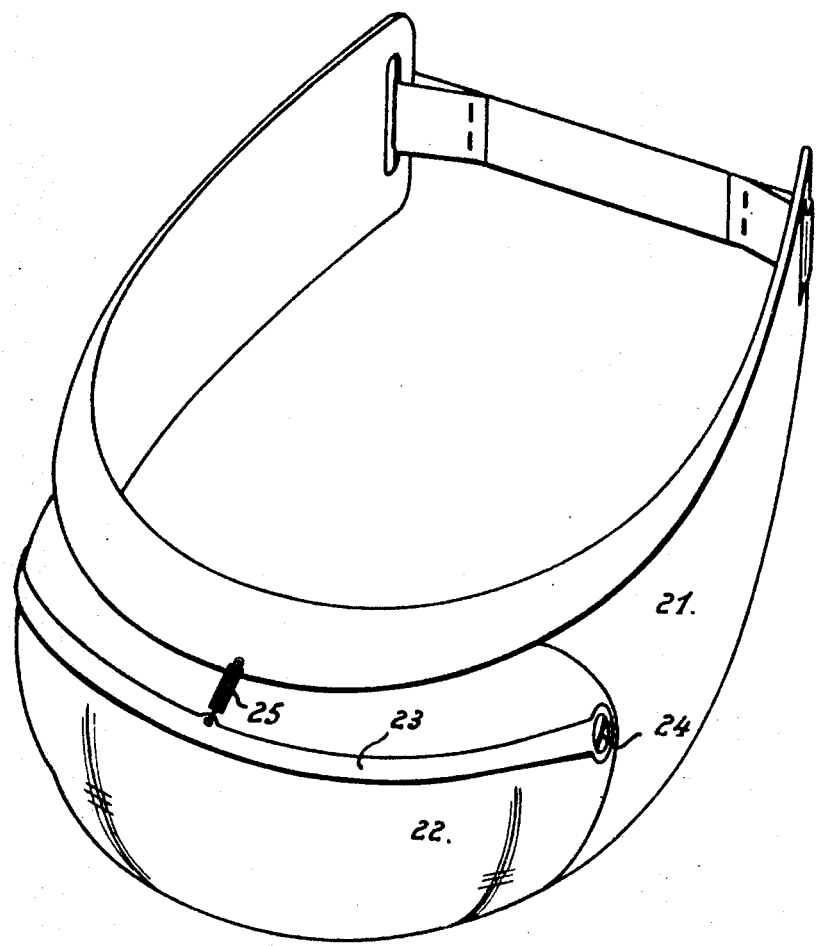
FIG. 4 is a perspective view of a second embodiment.
Figure 5:
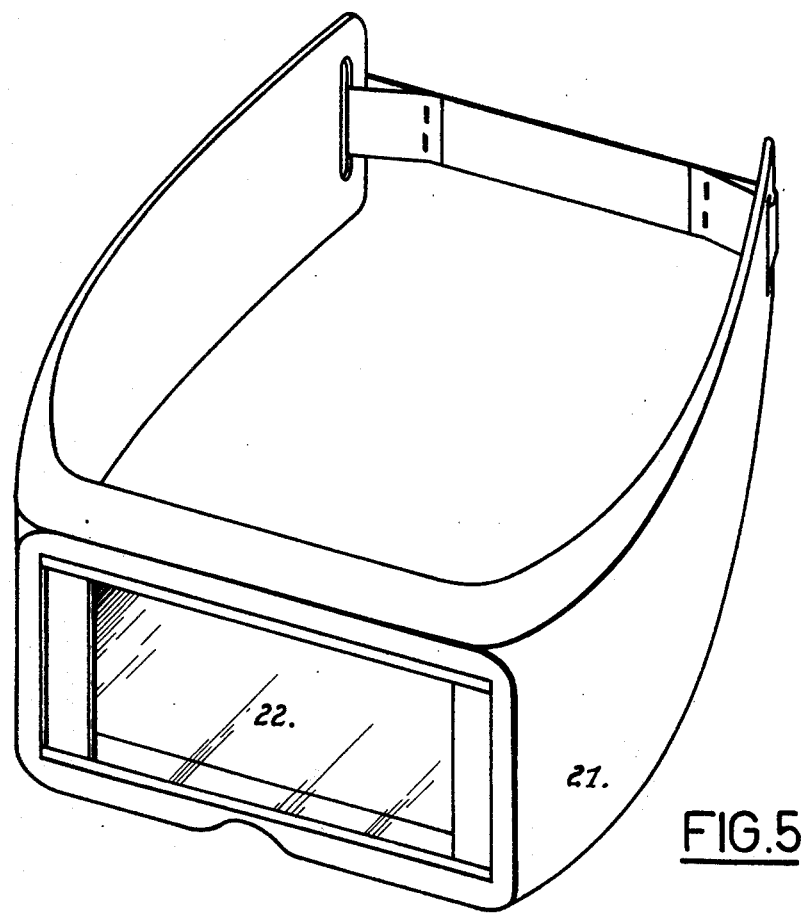
FIG. 5 is a perspective view of a third embodiment.
Figure 8:
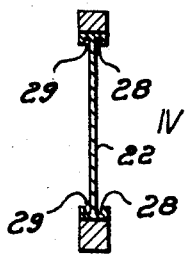
FIG. 8 is a cross section according line V—V of FIG. 6.
Figure 6:
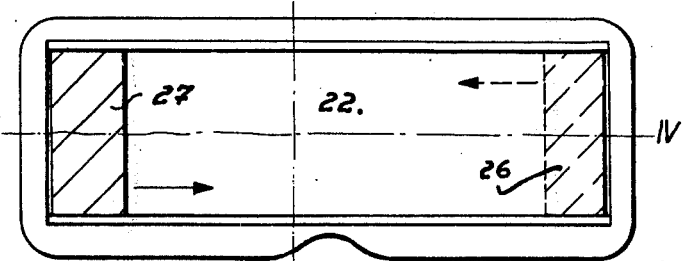
FIG. 6 is a front view of the glasses shown in FIG. 5.
Figure 7:
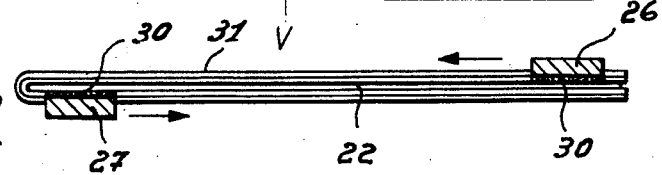
FIG. 7 is a cross section according to line IV—IV of FIG. 6.

In the second embodiment shown in FIG. 4, the protection glasses comprise a frame 21 made out of one portion forming the sides of the glasses and carrying a transparent screen 22 which is curved in its frontal portion. The rear free ends of the frame are connected by a resilent band.

A movable member 23 or wiper has the same shape as the screen and is pivoted at each of its ends on said screen or on the frame 24.

This wiper may, during its pivoting, sweep the screen from the top to the bottom. A spring 25 maintains this wiper 23 in its upper rest position. This spring may for example be placed in the hinge.

The face of this wiper 23 which is turned toward the screen 22 is provided with a cleaning device, for example constituted by a strip of expanded synthetic material. Therefore, when the user pulls the wiper down it causes a cleaning and a wiping of the screen 22.

In the third embodiment shown in FIGS. 5 to 8 the glasses comprise also a frame 21 carrying a screen 22 which is either plane or curved in its frontal portion. This screen is provided with two riders 26, 27, the one located against the inner face of the screen and the other against the outer face of the screen. These riders are slidingly mounted in grooves 28, 29 which are provided along the upper and lower edges of the screen.

Each rider is provided with a cleaning device 30 which may be constituted as described in the first embodiment.

In rest position the outside rider 27 is located for example as shown at the left end of the screen 22, whereas the internal rider 26 is located at the right end of this screen. The two riders 26, 27 are connected by one or two supple connecting members so that when the user displaces one of these rides, for example the outside rider, the other one, the inside rider, is automatically driven in a corresponding displacement of opposite direction.

Therefore in only one operation the inner and outer faces of the screen may be cleaned.

Figure 9:
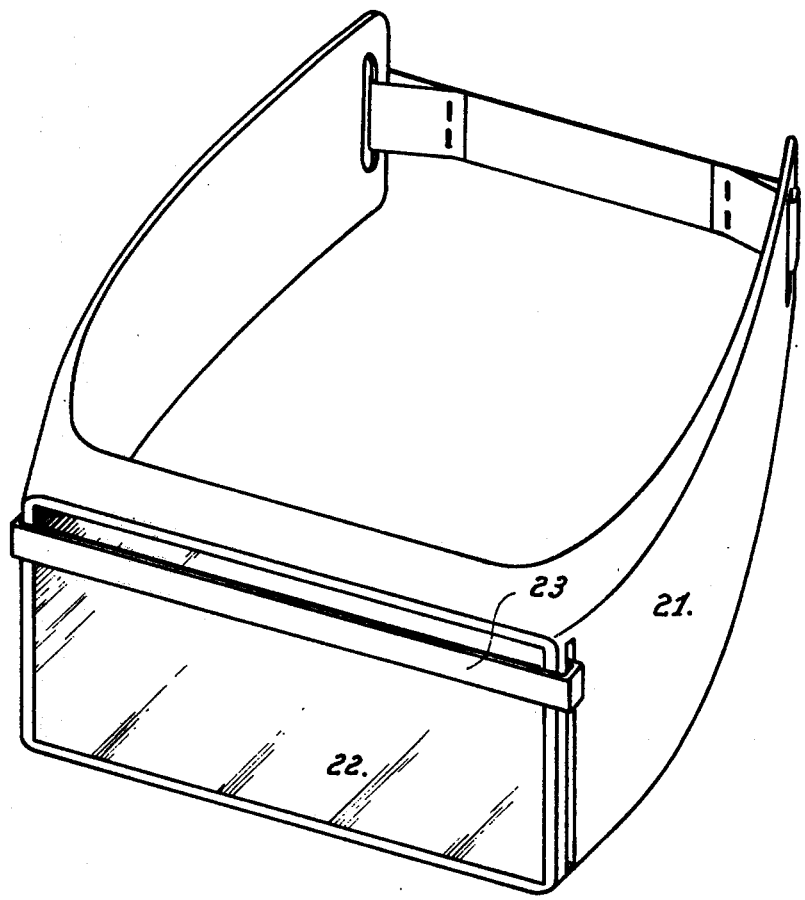
FIG. 9 is a perspective view of a fourth embodiment.

The fourth embodiment shown in FIG. 9 comprises also a frame 21 carrying a plane screen 22. A wiper 23 is slidingly mounted on this frame and displaces itself vertically in front of the screen 22. This wiper comprises also a cleaning device permitting one to wipe the screen during its displacements.

In a variant the wiper could be made of the form of a ring and to surround the screen 22. A cleaning of the two faces of the screen is thus obtained.

It is evident that for each embodiment the wiper may be provided with different variants of the cleaning device as described with respect to the first embodiment.

Finally the wiper or movable member could be driven in its displacements by means of a motor powered by battery and a mechanical transmission device.

Figure 10:
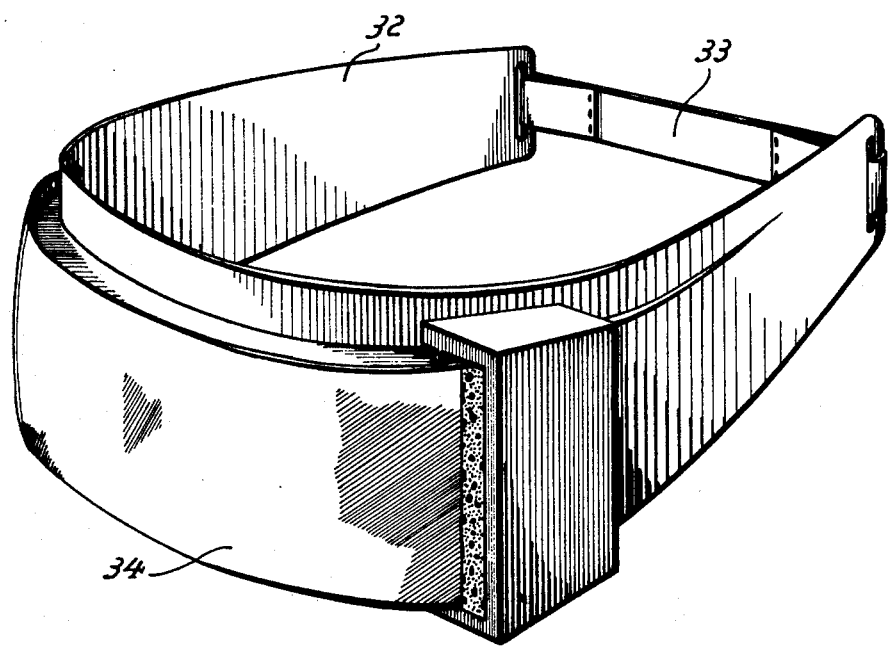
FIG. 10 shows a fifth embodiment of the protection glasses.
Figure 12:
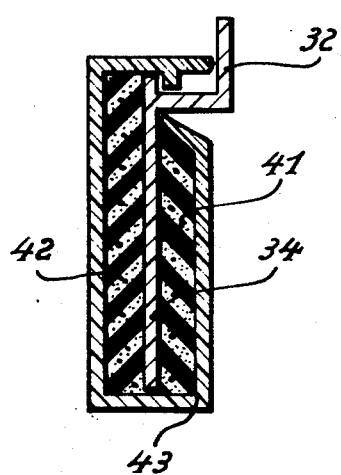
FIG. 12 is a cross section similar to the one shown in FIG. 11, of a variant of the movable member.
Figure 11:
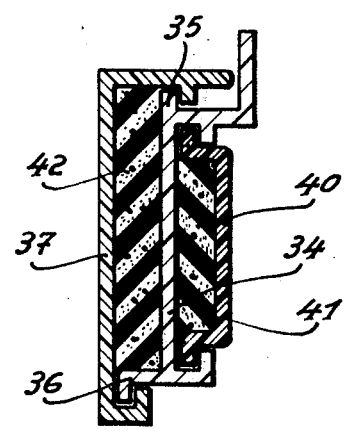
FIG. 11 is a cross section according to line X—X of FIG. 10.

In the fifth embodiment shown in FIGS. 10 to 12, the support as well as the screen are of only one piece and constitute together an assembly 32 the free ends of which are connected by means of a band 33 which is resilient or not.

The frontal portion 34 of the assembly 32 constitutes a transparent arcuate protective screen and has flanges 35, 36 forming slides for an outside rider 37. Between this frontal portion and the rider, a cleaning device 42 is located which is formed for example out of a portion of expanded plastic material.

The inside of this frontal portion 34 comprises also tow flanges 38, 39 constituting slides for an internal rider 40, which houses also a cleaning device 41.

The internal and outside riders are independent and permit one to clean independently the one or the other of the faces of the frontal transparent portion 34 constituting the screen.

In a variant shown in FIG. 12, the frontal portion 34 has a simple form and it is surrounded by only one rider 43, housing the two cleaning devices 41 and 42. In such a variant the rider could be constituted by a ring which would be completely closed on itself and surrounding the screen.

In this variant the user may in only one movement sliding the rider 43 on the screen 34, clean the two faces of said screen.

This fifth embodiment is extremely simple since it comprises only two moulded parts.

In both of the embodiments of FIGS. 11 and 12, as seen in FIG. 10, the protection glasses comprises an arcuate frame that at least partially encircles the head of the user, the screen being arcuate and integral with this frame. The screen has at least one flange 44 along at least one of the horizontal edges thereof, the wiping member having a flange 45 that engages with screen flange 44. More particularly, screen flange 44 defines with an edge portion of the screen an outwardly opening arcuate horizontal trough 46, wiping member flange 45 being slidably seated in trough 46. That edge portion of the screen that helps define trough 46 is flange 35 in FIG. 11 and flange 47 in FIG. 12.

Figure 13:
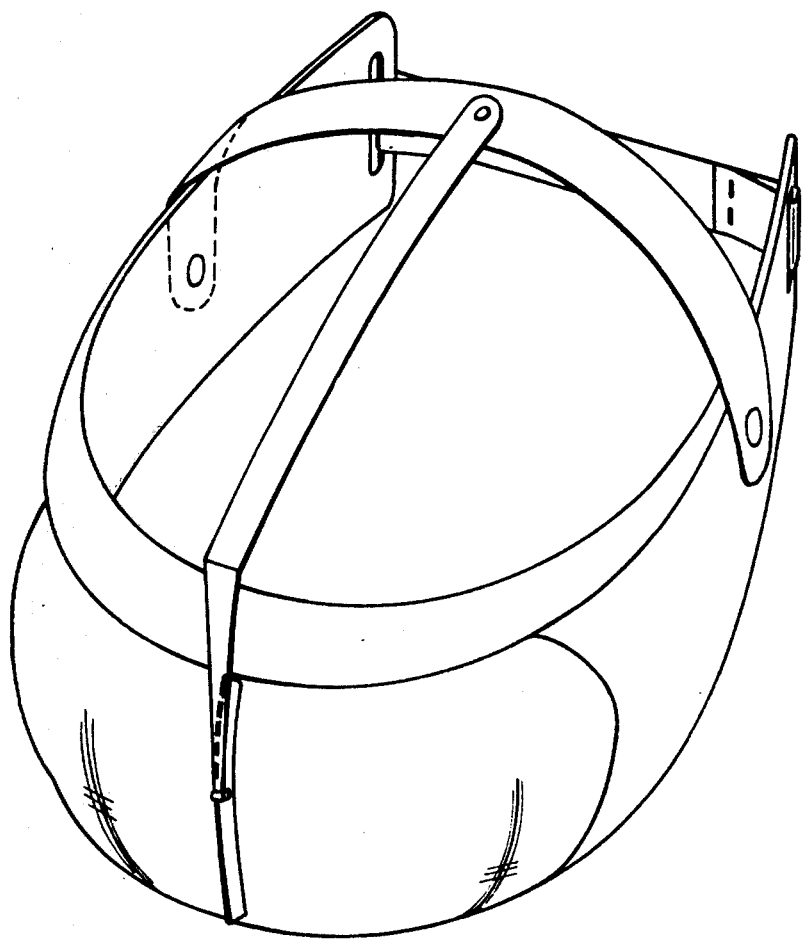
FIG. 13 shows another variant of the glasses.

In a variant shown in FIG. 13, the movable member may be constituted by a wiper pivoted on an axis which is fast on the support of the glasses. This wiper comprises a cleaning blade coming in contact with the screen and wiping a portion of it during the displacement, which can be continuous or reciprocating, of the movable member. The driving of the movable member in its angular displacements may be manual or provided by means of a motor powered by batteries for example.

I claim:
1. Protection glasses comprising a screen which is at least partially transparent, the screen having upper and lower substantially horizontal edges, and at least one movable wiping member that wipingly engages at least one face of said screen, and means mounting said wiping member slidable to engage said upper and lower edges of said screen thereby releasably to retain said wiping member in horizontal sliding engagement with said screen, said protection glasses comprising an arcuate frame that at least partially encircles the head of the user, said screen being arcuate and integral with said frame, there being a said wiping member on each side of said screen thereby to wipe both the inner and the outer faces of said screen, said screen having at least one flange along at least one said horizontal edge thereof, said wiping member having a flange that engages with said screen flange, said screen flange defining with an edge portion of said screen an outwardly opening arcuate horizontal trough, said wiping member flange being slidably seated in said trough.

2. Protection glasses as claimed in claim 1, said wiping members being separate from each other.

3. Protection glasses as claimed in claim 1, said wiping members being both mounted in a common frame for simultaneous movement along both sides of said screen.

4. Protection glasses as claimed in claim 1, said screen having flanges along both of said horizontal edges thereof, said wiping member having flanges that engage with said screen flanges.

5. Protection glasses as claimed in claim 1, said wiping member comprising a member that embraces said upper and lower edges of said screen and that has a pad of wiping material between said member and said screen.

* * * * *